United States Patent [19]

Hwa et al.

[11] Patent Number: 5,051,532
[45] Date of Patent: Sep. 24, 1991

[54] N,N-BIS-PHOSPHONOMETHYL TAURINE N-OXIDE AND WATER-SOLUBLE SALTS THEREOF

[75] Inventors: Chih M. Hwa, Palatine; John A. Kelly, Drystal Lake, both of Ill.; Janet Neton, West Chester, Ohio; Patricia M. Scanlon, Arlington, Mass.; Roger R. Gaudette, Hudson, N.H.

[73] Assignee: W. R. Grace & Co.-Conn., New York, N.Y.

[21] Appl. No.: 451,670

[22] Filed: Dec. 15, 1989

[51] Int. Cl.$^5$ ................................................ C07F 9/38
[52] U.S. Cl. ..................................... 562/12; 210/700; 252/82
[58] Field of Search .......................................... 562/12

[56] References Cited

U.S. PATENT DOCUMENTS

| | | | |
|---|---|---|---|
| 2,964,549 | 12/1960 | Ramsey et al. | 260/438 |
| 3,214,454 | 10/1965 | Blaser et al. | 260/429.9 |
| 3,336,221 | 8/1967 | Ralston | 210/58 |
| 3,474,133 | 10/1989 | Crutchfield et al. | 260/502.5 |
| 4,216,163 | 8/1980 | Sommer et al. | 260/502.5 |

FOREIGN PATENT DOCUMENTS

| | | | |
|---|---|---|---|
| 513981 | 10/1976 | U.S.S.R. | 562/12 |
| 666181 | 6/1979 | U.S.S.R. | 562/12 |

OTHER PUBLICATIONS

"Cyclishe Intramolekulare Ester von Athanolamin-N-methylenphosphonsauren", Worms et al., Zeitschrift fur Anorganische und Allgemeine Chemie, Band 381, 1971; pp. 260-265.

"The Direct Synthesis of α-Amino-methylphosphonic Acids", Moedritzer et al., Mannich-Type Reactions with Orthophosphorous Acid, May 1966, pp. 1603-1607.

"Hydrogen Peroxide Oxidation of Tertiary Amines", Hoh et al., Journal of the American Oil Chemists' Soceity, Jul. 1963 Issue vol. LV, No. 7, pp. 268-271.

"Recent Advances in Fatty Amine Oxides. Part I. Chemistry and Preparation", Lake et al., Journal of the American Oil Chemists' Society, Nov. 1963 Issue, vol. 40, No. 11, pp. 628-631.

"Analysis of Reaction Mixtures from the Hydrogen Peroxide Oxidation of Dimethyldodecylamine by the Preferred Method", Dupont Technical Information.

"Detoxication Mechanisms. II. The Iron Catalyzed Dealkylation of Trimethylamine Oxide", Ferris et al., Journal of the American Chemical Society/89:20/Sep. 27, 1967, pp. 5270-5275.

Kirk-Othmer, Encylopedia of Chemical Technology, Third Edition, vol. 2, p. 259, John Wiely & Sons, New York, 1978-Amine Oxides.

"Chlorine-resistant, Sequestering-dispersing Agent-"-Sequion OA, Giovanni Bozzetto, pp. 10-12.

Primary Examiner—J. E. Evans
Attorney, Agent, or Firm—James P. Barr

[57] ABSTRACT

This invention relates to novel organic phosphonate compounds which can be used as water treatment agents. More specifically, this invention relates to the compound N,N-bis-phosphonomethyl taurine N-oxide which may be represented by the formula:

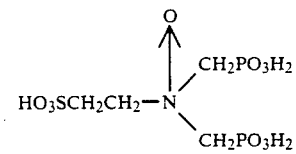

and its water soluble salts, which can be employed for the control of scale and/or corrosion.

2 Claims, No Drawings

N,N-BIS-PHOSPHONOMETHYL TAURINE N-OXIDE AND WATER-SOLUBLE SALTS THEREOF

FIELD OF THE INVENTION

This invention relates to organic phosphonate compounds and more particularly to organic phosphonates which can be used as water treatment agents.

BACKGROUND OF THE INVENTION

Much recent research has concerned development of organic water treatment agents for use in scale or corrosion control. Organic corrosion inhibitors which can reduce reliance on the traditional inorganic inhibitors are particularly sought. Among the organic agents successfully employed for water treatment are numerous organic phosphonates. These compounds may generally be employed without detrimentally interfering with other commercial water treatment additives. Phosphonic acid compounds have also been used in other fields for such purposes as flame retardants, plasticizers, lubricants and surfactants.

U.S. Pat. No. 3,214,454 to Blaser et al discloses certain acylation products of phosphorous acid (e.g. hydroxyethylidene diphosphonic acid) and use thereof as complex formers for metal ions (e.g. calcium). Delay of calcite precipitation by the use of substoichiometrical amounts of the compounds is disclosed, as is the comparative effectiveness of certain products in preventing scale formation (e.g. in boilers, tubes, etc.).

U.S. Pat. No. 3,336,221 to Ralston discloses that compounds having a methylphosphonic acid (or alkali metal or ammonium salts thereof) bonded to a nitrogen atom (e.g. pentasodium amino tri(methyl phosphonate) and phosphonomethyl ethanolamines) are threshold active compounds, useful for inhibiting the precipitation of various scale-forming compounds (e.g. calcium carbonate).

U.S. Pat. No. 3,474,133, U.S. Pat. No. 3,470,243, and U.S. Pat. No. 3,429,914 all to Crutchfield et al., disclose that certain organo-phosphono-amine oxide compounds can be prepared by oxidizing organo-phosphono amine with a suitable oxidizing agent. For instance ethanol bis(dihydrogen phosphonomethyl) amine can be reacted with $H_2O_2$ to yield ethanol bis(dihydrogen phosphonomethyl) amine oxide (i.e. $HOCH_2CH_2N(O)(CH_2PO_3H_2)_2$); and tris(dihydrogen phosphonomethyl) amine can be reacted with $H_2O_2$ to yield tris(dihydrogen phosphonomethyl) amine oxide (i.e. $ON(CH_2PO_3H_2)_3$). It is disclosed that the organo-phosphono amine oxides have utility in practically all fields of organic chemistry wherein their acidic or salt and/or amine oxide properties can be utilized; and the various utilities indicated for the compounds in such fields include utility as sequestering or chelating agents, water treating agents, stabilizers for peroxy compounds and corrosion inhibitors. In particular, the acids and water soluble salts of the tris(phosphono lower alkylidene) amine oxides are reported to exhibit the property of being effective sequestering agents for metal ions in alkaline mediums. For example, the penta sodium salt of tris(dihydrogen phosphonomethyl) amine oxide is reported to sequester calcium ions in alkaline media in over a mole per mole basis.

U.S. Pat. No. 4,216,163 to Sommer et al. discloses certain N-sulfo alkane amino alkane phosphonic acids which can be produced by reacting an alkali metal salt of an amino phosphonic acid with a halo or hydroxyalkane sulfonic acid in an alkaline medium, their high resistance against hydrolysis at high temperatures, their very high water solubility, their suitability as complexing or sequestering agents especially with respect to polyvalent metal ions, and their use in substoichiometric amounts to stabilize the hardness of aqueous media, and their advantageous use for preventing scale and deposit formation in aqueous systems as they are employed for instance in textile bleaching baths, in water used for sterilizing cans, for preventing the formation of resinous deposits in the manufacture of paper, and the like. For example, sodium isethionate is reacted with imino bismethane phosphonic acid (and sodium hydroxide) to yield N,N-bis-phosphonomethane amino ethane sulfonic acid with a thin-layer chromatogram corresponding to that of the product which is obtained on phosphono methylation of taurine by means of phosphorous acid and formaldehyde.

While as indicated above, various phosphonates have proved useful for particular water treatment applications, many of them nevertheless have important disadvantages when treating water under certain conditions. For example, many phosphonates such as tri(methylphosphonic acid) are not chlorine resistant and thus degrade in the presence of free chlorine which is commonly used as a disinfectant or biocide in many aqueous systems. Other phosphonates including tri(phosphono lower alkylidene) amine oxide compounds such as tris(dihydrogen phosphonomethyl) amine oxide are considered very sensitive to calcium hardness and are prone to form calcium phosphonate precipitates. There is thus a continuing need for safe and effective water treating agents which are sufficiently versatile to be used when substantial calcium and/or free chlorine is present in the water to be treated.

SUMMARY OF THE INVENTION

N,N-Bis-phosphonomethyl taurine N-oxide and its water soluble salts are disclosed in accordance with this invention. These compounds are particularly useful as water treatment agents which can be employed for the control of scale and/or corrosion.

It is an object of this invention to provide a water treatment agent useful for corrosion and/or scale control.

It is another object of this invention to provide a water treatment agent which is considered calcium insensitive.

It is yet another object of this invention to provide a water treatment agent which is resistant to free chlorine in water.

These and other objects and advantages of the present invention will become apparent from the detailed description of the invention which follows.

DETAILED DESCRIPTION OF THE INVENTION

This invention relates to the compound N,N-bis-phosphonomethyl taurine N-oxide and its water soluble salts. N,N-Bis-phosphonomethyl taurine N-oxide may be represented by the general formula

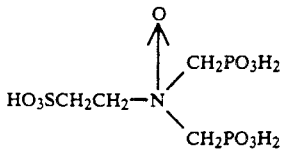

N,N-bis-phosphonomethyl taurine N-oxide may be prepared by conventional oxidation of the trisubstituted nitrogen of the tertiary phosphonomethyl amine, N,N-bis-phosphonomethyl taurine with a suitable oxidizing agent. Suitable oxidizing agents are generally oxidizing agents which contain an O—O linkage (peroxide compound) and have oxidizing action. Suitable oxidizing agents are considered to include hydrogen peroxide, substituted peroxides and additional compounds of hydrogen peroxide such as the peroxide of sodium and the peroxide of potassium, urea percompounds, percarbonates, perborates, persulfates and the peracids such as persulfuric acid, peracetic acid, peroxymonophosphoric acid and the like as well as their water-soluble salt compounds such as sodium, potassium, ammonium and organic amine salts. In general, the oxidation process is usually carried out in an aqueous medium.

Hydrogen peroxide is the preferred oxidizing agent. Reference is made to Hoh et al. "Hydrogen Peroxide Oxidation of Tertiary Amines", The Journal of the American Oil Chemists' Society, Vol. LV, No. 7, pp 268-271 (July 1963) and Lake et al. "Recent Advances in Fatty Amine Oxides. Part I. Chemistry and Preparation", The Journal of the American Oil Chemists' Society, Vol. 40, No. 11, pp. 628-631 (November 1963) for discussion of such oxidations. In general, a solution of the tertiary amine may be advantageously reacted at a pH of about 10 with about 20% excess hydrogen peroxide. It is preferred to use concentrations of hydrogen peroxide above about 2% by weight of the reaction medium.

The water soluble salts are readily prepared from N,N-bis-phosphonomethyl taurine N-oxide by neutralizing the phosphonic acid group with a stoichiometric amount of a base or salt that contains essentially the desired cation or by conversion of N,N-bis-phosphonomethyl taurine to a salt form prior to its oxidation to the amine oxide. Bases and salts of acids such as those containing an alkali metal, alkaline earth metal, zinc, aluminum, ammonia and amines are especially suited, with sodium and potassium salts being preferred. For example, to make a sodium salt, a free acid of N,N-bis-phosphonomethyl taurine N-oxide can be neutralized with a stoichiometric amount of a base containing sodium cation, such as sodium hydroxide.

Other bases or salts which can be reacted with the free acids to produce salt compounds of the instant invention include the inorganic alkali metal salts, oxides and hydroxides such as $Na_2O$, $Na_2CO_3$, $KOH$, $K_2O$, $K_2CO_3$, $LiOH$, $Li_2CO_3$, $CsOH$, $Cs_2CO_3$, other inorganic salts, and hydroxides such as $Al(OH)_3$, $Al_2(SO_4)_3$, $Al(NO_3)_3$ and $ZnSO_4$ and amines, particularly low molecular weight amines (i.e. amines having a molecular weight below about 300), and more particularly the alkyl amines, alkylene amines and alkanol amines containing not more than 2 amine groups such as ethyl amine, diethylamine, propyl amine, propylene diamine, hexylamine, 2-ethyl hexylamine, N-butylethanol amine, triethanolamine and the like.

The tertiary phosphonomethyl amine, N,N-bis-phosphonomethyl taurine which is useful as a reagent for preparing the compounds of the instant invention can be prepared by the known reaction of a nitrogenous material (i.e. taurine; $H_2N$-$CH_2CH_2SO_3H$) with a compound containing a carbonyl group (i.e. formaldehyde) and orthophosphorous acid. Reference is made to U.S. Pat. No. 4,216,163 which is hereby incorporated herein in its entirety by reference, for guidance in reacting imino bis-methane phosphonic acid, sodium hydroxide and sodium isethionite to yield a corresponding product.

For the foregoing methods of preparation, reaction conditions such as temperatures, pH and time for reaction can be varied with the optimum conditions for the reactions being readily ascertained by those skilled in the art. Reference is made to U.S. Pat. No. 3,429,914, which is hereby incorporated herein in its entirety by reference, for a discussion of the preparation of organo-phosphono amines and organo-phosphono-amine oxides.

N,N-bis-phosphonomethyl taurine N-oxide and its water soluble salts are useful in water treatment applications. It has been found that the compounds of this invention can be used to inhibit corrosion of metals in aqueous systems as well as to inhibit the formation of scale in such systems. Thus, both the formation of scale and the corrosion of metals can be inhibited in an aqueous system by addition of the compounds of this invention to the system water. Moreover the compounds of this invention are calcium insensitive and resistant to free chlorine in aqueous solution. In addition metal surfaces can be passivated by N,N-bis-phosphonomethyl taurine N-oxide. Accordingly the compounds of this invention are considered particularly versatile water treatment agents.

Practice of the invention will become further apparent from the following non-limiting examples.

EXAMPLE I

To a solution of taurine (215 grams, 1.7 mole) in water (700 ml), phosphorous acid (100%, 287 grams, 3.5 mole) was added slowly followed by concentrated hydrochloric acid (36%, 250 ml). The solution was heated with stirring to 100° C., and formaldehyde (36%, 388.5 grams, 4.66 mole) was added dropwise at 100°-105° C. during 2½ hours. The solution was refluxed for 4½ hours and then concentrated in a rotary evaporator to a thick clear liquid. Analysis of the $P^{31}NMR$ spectra of the product indicates N,N-bis-phosphonomethyl taurine.

EXAMPLE II

To a cooled solution of N,N-bis-phosphonomethyl taurine (69.63 grams, 0.222 mole) in water (32.77 grams), sodium hydroxide solution (50%, 94.19 grams, 1.18 mole) was added very slowly until pH 10.0 was obtained. To this solution, hydrogen peroxide solution (35%, 25.94 grams, 0.2670 mole) was added dropwise. After the addition was over, the resultant solution was stirred at ambient temperature for 20 hours. Analysis of the $P^{31}NMR$ spectra of the product indicates N,N-bis-phosphonomethyl taurine N-oxide.

EXAMPLE III

The calcium sensitivity for N,N,-bis-phosphonomethyl taurine N-oxide was tested using a cloud point test wherein the phosphonomethyl amine oxide was added to a 250-ml beaker containing a hard water solution having a temperature of 60° C., having a pH of 8.3, and containing 500 ppm calcium ion (as CaCO$_3$) and 0.005M borate buffer. Over 100 ppm of N,N-bis-phosphonomethyl taurine N-oxide was added without reaching a cloud point (i.e. a point at which the solution becomes turbid). Accordingly the N,N-bis-phosphonomethyl taurine N-oxide was considered "calcium insensitive".

It is noted that not all phosphonates, nor even all organo phosphono amine compounds exhibit the calcium insensitivity of N,N-bis-phosphonomethyl taurine N-oxide. For example, the addition of about 5 ppm amino tri(methylphosphonic acid) N-oxide or the addition of about 7 ppm hydroxyethylidene diphosphonic acid each produces a cloud point in the cloud point test described in Example III.

EXAMPLE IV

A test solution was formulated to approximate a 4-fold concentrate of Chicago tap water. The water had an initial pH of about 8.5. Two mild steel coupons were weighed and suspended for three days in an air-sparged sample of the solution at 54° C. The steel coupons were then removed and reweighed, and an average corrosion rate (in mils per year) over the three days was calculated on the basis of coupon weight loss. The results are provided in Table A below (Run 1). Three additional runs (Runs 2, 3 and 4) were made using the same procedure except that 15 ppm, 30 ppm, and 45 ppm of N,N-bis-phosphonomethyl taurine N-oxide were respectively added to the test solution. The calculated coupon corrosion rates for these runs are also shown in Table A below.

TABLE A

| Run | Additive | Additive Concentration(ppm) | Corrosion Rate (mpy) |
|---|---|---|---|
| 1. | None | — | 48.0 |
| 2. | N,N-Bis-phosphono-methyl taurine N-oxide | 15 | 10.4 |
| 3. | N,N-Bis-phosphono-methyl taurine N-oxide | 30 | 5.0 |
| 4. | N,N-Bis-phosphono-methyl taurine N-oxide | 45 | 3.0 |

There was no pH control during the test of this example and the final pH of the test solutions after the three day test ranged from about 8.8 to 9.5.

EXAMPLE V

A potentiodynamic polarization test was conducted for demonstrating passivation by a solution of 30 ppm N,N-bis-phosphonomethyl taurine N-oxide. In this test a disc of 1010 mild steel was polished to 600 grit finished, ultrasonicly cleaned in soap water, and rinsed with acetone. The solution was subjected to argon de-aeration to achieve an oxygen concentration of less than 0.5 ppm. The solution was adjusted to a pH of 8.5 by using sodium hydroxide or hydrochloric acid and heated to 55° C. by a water bath. The disc surface is reduced for 200 seconds at −1 volt against saturated calomel electrode. During the potentiodynamic polarization measurements, the potential is swept at 1 millivolt per second.

The tabularized results for these runs are shown in Table B below.

TABLE B

| Potential (E) (Volts/Saturated Calomel Electrode) | Current Density (I) (Amperes/Square Meter) N,N-Bis-phosphonomethyl taurine N-oxide (30 ppm) |
|---|---|
| −0.99 | 2.52 |
| −0.95 | 1.70 |
| −0.90 | 0.90 |
| −0.86 | 0.53 |
| −0.81 | 0.20 |
| −0.76 | 0.01 |
| −0.70 | 0.12 |
| −0.66 | 0.19 |
| −0.60 | 0.26 |
| −0.55 | 0.28 |
| −0.50 | 0.30 |
| −0.46 | 0.35 |
| −0.41 | 0.41 |
| −0.35 | 0.57 |
| −0.30 | 0.96 |
| −0.25 | 1.92 |
| −0.20 | 4.64 |
| −0.15 | 9.35 |
| −0.10 | 15.07 |
| −0.06 | 25.5 |
| −0.02 | 33.0 |

An interval of relatively constant current density over a range of potential is considered indicative of passivation. The current density over the potential range of −0.60 to −0.50 is considered indicative of passivation of metal surfaces in the presence of N,N-bis-phosphonomethyl taurine N-oxide.

EXAMPLE VI

A two ppm solution of N,N-bis-phosphonomethyl taurine N-oxide in zero hardness water was heated for 24 hours at 60° C. The amount of organic phosphonate which was converted to orthophosphate was then determined. Additional runs (runs 2 and 3) were made using the same solution except that 10 ppm and 20 ppm of NaOCl were respectively added prior to heating. The results are shown in Table C below.

TABLE C

| Run | Additive | NaOCl Added (ppm) | % Conversion |
|---|---|---|---|
| 1 | N,N-Bisphosphonomethyl taurine N-oxide | 0 | 5.8 |
| 2 | N,N-Bisphosphonomethyl taurine N-oxide | 10 | 13.6 |
| 3 | N,N-Bisphosphonomethyl taurine N-oxide | 20 | 14.7 |

For comparison, N,N-bis-phosphonomethyl ethanolamine and amino tri(methylphosphonic acid) showed 100% and 93% conversion, respectively, under the above testing conditions in the presence of 10 ppm NaOCl. Unlike N,N-bis-phosphonomethyl ethanolamine and amino tri(methylphosphonic acid), the N,N-bis-phosphonomethyl taurine N-oxide of the instant invention is chlorine resistant.

EXAMPLE VII

The ability of the calcium insensitive phosphonomethyl amine oxide, N,N-bis-phosphonomethyl taurine N-oxide, to also inhibit calcium carbonate formation was demonstrated using a threshold inhibitor test. In this test 800 ml of a test solution containing 400 ppm calcium (as Ca) and 400 ppm bicarbonate (as HCO$_3$) in a 1000 ml beaker was stirred with a magnetic stir bar and heated using a stainless steel immersion heater to 49° C. The pH was monitored during heating and kept at pH 7.15 with addition of dilute HCl. After the temperature of 49° C. was achieved, 0.1N NaOH was added to the test solution at a rate of 0.32 ml/min using a syringe pump and the rise in pH was monitored. A decrease or plateau in the rate of pH increase is observed when calcium carbonate starts to precipitate, and the pH at which this decrease or plateau is observed is termed the critical pH. The critical pH for the test solution is shown in Table D below along with the total milliequivalents per liter of hydroxide (as NaOH) added to reach the critical pH.

The procedure was repeated using test solution to which 5 ppm of the calcium insensitive N,N-bis-phosphonomethyl taurine N-oxide was added. A run is also shown for amino tri(methylphosphonic acid) N-oxide which as indicated above is considered calcium sensitive when compared to N,N-bis-phosphonomethyl taurine N-oxide. The results are shown in Table D below.

TABLE D

| Run | Additive | Critical pH | NaOH added to reach critical pH (meq/l) |
|---|---|---|---|
| 1 | Blank (without treatment) | 7.69 | 0.48 |
| 2 | N,N-Bis-phosphonomethyl taurine N-oxide | 8.89 | 2.49 |
| 3 | Amino tri(methylphosphonic acid) N-oxide | 8.50 | 1.34 |

As shown in Table D, use of the phosphonomethyl amine oxide of the present invention raised the critical pH and generally resulted in substantially more sodium hydroxide addition before the critical pH was reached. This phosphonomethyl amine oxide is thus an effective threshold inhibitor, capable of inhibiting calcium carbonate precipitation.

EXAMPLE VIII

Scale formation was further tested using an apparatus comprising a covered 28-liter basin, a centrifugal pump which withdraws liquid from the bottom of the basin and circulates it through tubing respectively to a needle valve which allows flow control, a flow meter which allows flow measurement, a glass housing containing an immersion heater for heating the liquid which is returned to the basin. A cooling coil is provided in the basin and is connected such that tap water may be circulated through the cooling coil. The liquid temperature is controlled using a thermoregulator which activates a solenoid valve which controls the flow of tap water through the coil. A pH probe is also located in the basin and is operably connected to a pH controller which in turn controls a pair of solenoid valves which respectively control flow of 0.5N NaOH and 0.2N H$_2$SO$_4$ from 1-liter containers to the basin.

Five liters of test solution containing 600 ppm total hardness (as CaCO$_3$) was transfered to the basin and circulated at a flow rate of 1.4 ft. per second using the centrifugal pump. The pH was controlled within the range of 8.0-8.2 and the variable transformer was turned on such that the heat flux for the immersion heater was 10.9 KBTU per square foot per hour. The cooling coil was operated such that the outlet water from the basin was controlled at 60° C. After six hours the power transformer and the pH controller were turned off and the pH probe was removed from the basin. The water in the basin was cooled rapidly by resetting the thermoregulator to provide tap water circulation through the cooling coil. A sample of test solution was removed from the basin when it had cooled to 35° C., and it was analyzed for total hardness. The results are shown in Table E below. The reduction in total hardness was considered indicative of the scale formation in the system.

The run was repeated using the above procedure except that 2 ppm N,N-bis-phosphonomethyl taurine N-oxide was added to the solution prior to heating. The total hardness of the test solution at the conclusion of these runs are shown in Table E below, as is the reduction in total hardness, and the calculated inhibition of scale formation.

TABLE E

| Run | Additive | Test Solution Total Hardness (ppm) | | | Calculated Scale Inhibition % |
|---|---|---|---|---|---|
| | | Start | End | Change | |
| 1 | Blank (without treatment) | 600 | 134 | 466 | — |
| 2 | N,N-Bis-phosphonomethyl taurine N-oxide (2 ppm) | 600 | 599 | 1 | 99.8 |

The Examples encompass particular embodiments of the invention. Other embodiments will become apparent to those skilled in the art from a consideration of the specification or practice of the invention disclosed herein. It is understood that modifications and variations may be produced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A compound of the formula

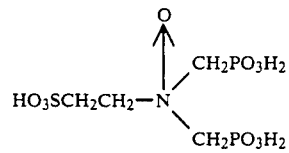

and water soluble salts thereof.

2. A compound according to claim 1 wherein the compound is selected from N,N-bis-phosphonomethyl taurine N-oxide and its sodium and potassium salts.

* * * * *